Feb. 6, 1973 W. E. DUFFETT Plant Pat. 3,299
CARNATION PLANT
Filed June 15, 1971 2 Sheets-Sheet 1
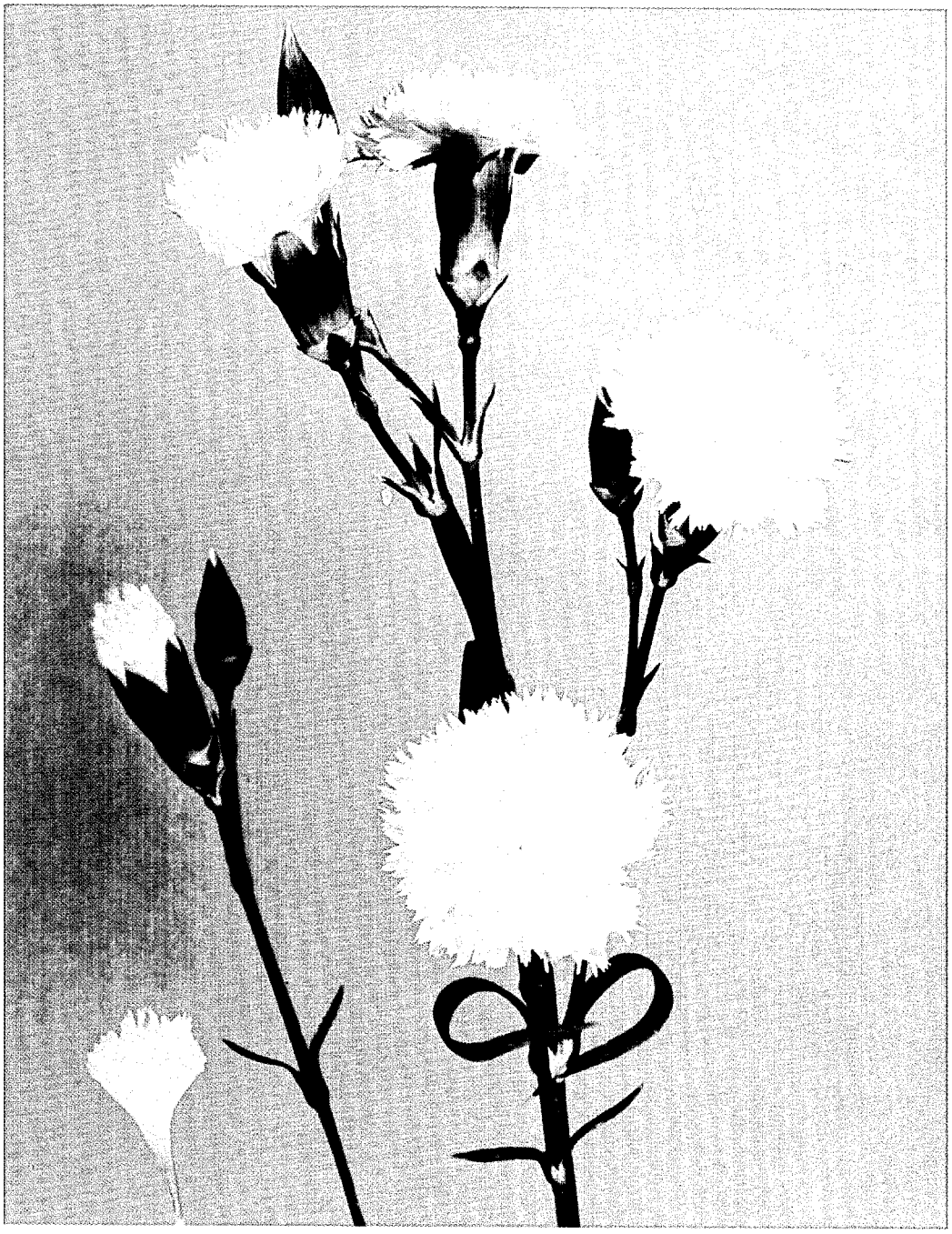
INVENTOR
WILLIAM E. DUFFETT
BY Oberlin, Maky, Donnelly & Renner
ATTORNEYS CARNATION PLANT
Filed June 15, 1971 2 Sheets-Sheet 2
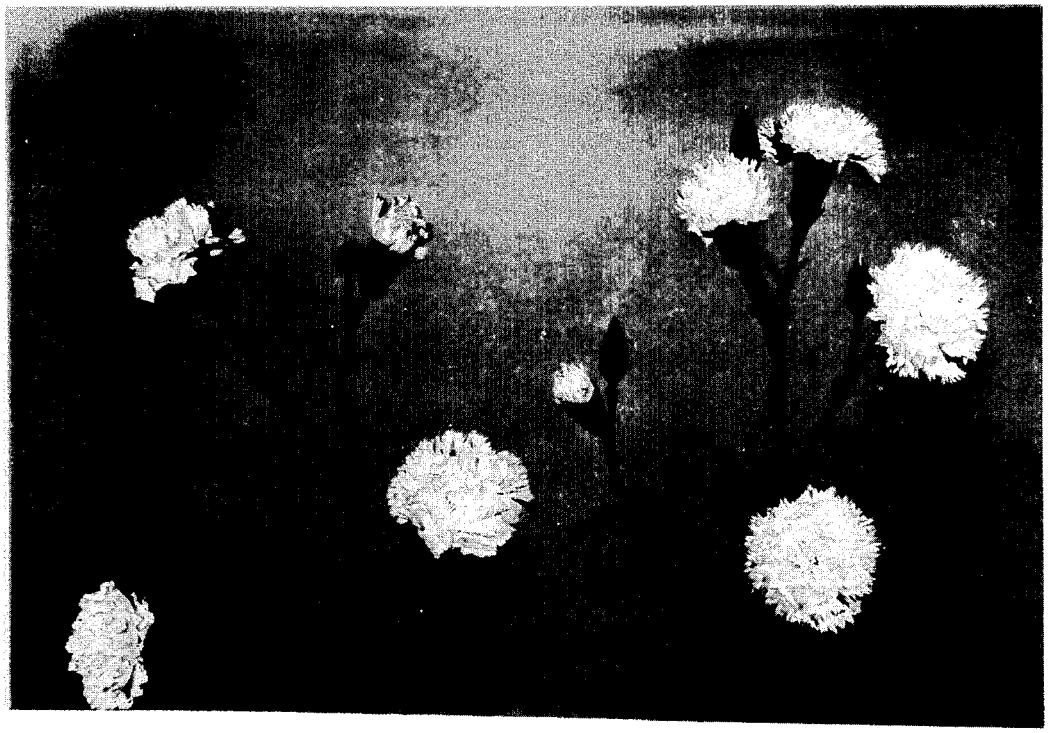

United States Patent Office

Plant Pat. 3,299
Patented Feb. 6, 1973

3,299

CARNATION PLANT

William E. Duffett, Akron, Ohio, assignor to Yoder Brothers, Inc., Barberton, Ohio

Filed June 15, 1971, Ser. No. 153,458
Int. Cl. A01h *5/00*
U.S. Cl. Plt.—70 1 Claim

The present invention comprises a new and distinct cultivar of carnation plant which is a seedling of parents identified as #145×#1286. Both parents are unpatented and are identified by the above numbers for breeding purposes.

The new cultivar is similar in many respects to the unpatented, commercial cultivar White Elegance, having the same characteristics as White Elegance of:

(1) A spray type or white miniature cultivar.

(2) Continuity of year round, perpetual flowering.

The new cultivar is distinguished from White Elegance by the following characteristics, when grown under comparable conditions:

(1) Lighter foliage color on new growth.

(2) Plants have six to ten inches more vigor, averaging seven inches taller than White Elegance.

(3) Stem length averages two inches longer.

(4) Averages two to four more flowers and buds per stem, which enables it to grade out 5–10% higher on the top two grades based on Society of American Florists grade standards. (See attached chart on page 6.)

(5) Responds or flowers approximately 7–10 days earlier on the first crop, from comparative flowerings planted and pinched on the same date.

(6) It produces well budded, open sprays during the winter months when White Elegance is very terminal at 54° F. minimum night temperature.

(7) Buds are longer and more pointed.

(8) Flower color is more ivory.

(9) One less sepal in the calyx (5 rather than 6).

(10) Two to five days longer keeping quality.

(11) A strong but pleasant fragrance. White Elegance has little or no fragrance.

(12) Flowers up to one quarter inch smaller in diameter.

(13) More fully petalled flowers, averaging approximately 50% more petals per flower.

(14) One-year crops planted after July 1, and into the winter months, will average 2–5 more stems per square foot because Ocean Spray will produce more breaks that develop into flowering stems on the return crop under the shorter days of fall and winter. One-year crops planted in the spring months, primarily May and June, result in near equal production per square foot because the number of breaks produced on the return crop are initiated during longer day length periods.

(15) A vegetative lateral shoot at the seventh node, develops in fall and winter, stopping about March 1.

The new cultivar has been asexually reproduced by cuttings at Salinas, Calif., and has been found to retain its distinctive characteristics through successive propagations.

The following detailed description is based on observations made of the new cultivar in a greenhouse in Salinas, Calif. The response time, blooming period, total vigor, and color may vary significantly with varying environmental conditions such as temperature, day length, and light intensity.

The accompanying drawings show the unique characteristics of the new cultivar, the color being as nearly true as possible with color illustrations of this type. Sheet 1 comprises a color photograph of the new cultivar and sheet 2 comprises a black and white comparison photograph, with the new cultivar appearing on the right and the comparison cultivar White Elegance appearing on the left. Certain of the above mentioned differences in characteristics between the respective cultivars will be apparent from the comparison photograph.

Color references are made to the Munsell Color Book, 1963 edition, and comparisons are made with the cultivar White Elegance.

Botanical classification.—*Dianthus caryophyllus longicaulis*

| | Ocean Spray | White Elegance |
|---|---|---|
| Bloom: | | |
| Type | Spray | Spray. |
| Size (diam. in inches) | 2" | 2¼". |
| Average number flowers and lateral buds per stem. | 9 | 6. |
| Petal edge | Serrated | Lightly serrated. |
| Petal count | 45 | 27. |
| Petal texture | Smooth | Smooth. |
| Petal size: | | |
| Average length | 1⅞" | 1⅞"–2". |
| Average width | 1" | 1". |
| Bud shape | Tubular pointed, cone shaped | Ovoid, narrow. |
| Splitting tendency | Up to 2% | None. |
| Slab tendency | None | Do. |
| Keeping quality | 9–12 days | 7–8 days. |
| Fragrance | Intense | Mild to none. |
| Color: | | |
| Center of flower | N9.5/white | N9.5/white. |
| Base of petals | 5GY9.2/yellow green | 5GY/light yellow green. |
| Inside of petals | N9.5/white | Lightly flushed purple blotches 7.5P6.6 light purple on white N9.5. |
| Reverse of petals | N9.5/white | N9.5/white. |
| Color stability | Stable | Stable. |
| Reproductive organs: | | |
| Stamen, anthers | 10YR8/2 yellow | 7.5P6/6, light purple. |
| Pollen | None | 7.5P7/2, light purple. |
| Stigma | N9.5/white | 7.5P6/6, light purple. |
| Styles | do | N9.5/white. |
| Length | 1¼" | ¾". |
| Ovaries | 5GY8/4, yellow green | 5GY, light yellow green. |
| Calyx: | | |
| Size | 1⅜" in length | 1⅛" in length. |
| Shape | Tubular, sharply pointed | Narrow bell shaped. |
| Number of sepals | 5 | 6. |
| Stems: | | |
| Length, average from a single pinch one-year crop. | 20" | 18". |
| Bending traits | 12 o'clock year round | 12 o'clock much of year, will weaken and bend to 3 o'clock in low light periods of winter. |

TABLE—Continued

| | Ocean Spray | White Elegance |
|---|---|---|
| Plant: | | |
| Form | Erect and branching bush | Erect and branching bush. |
| Growth | Vigorous, strong, sturdy, and upright. | Medium, strong, sturdy and upright. |
| Height, average from a single pinch one-year crop. | 32"-36" | 26"-28". |
| Foliage: | | |
| Topside (color) | 10GY3/4, deep green | 10GY3/4, deep green. |
| Underside (color | do | 10GY5/4, steel green. |
| Immature (color) | 10GY5/4, steel green | 10GY6/4, green. |
| Mature (color) | 10GY3/4, deep green | 10GY3/4, deep green. |
| Length mature leaf | 5.5" | 4.0"-4.5". |
| Shape | Long, narrow | Long, narrow. |
| Texture | Glaucous | Glaucous. |
| Displacement | Opposite | Opposite. |

The following table represents comparative production and grade data for the new cultivar and White Elegance, based on June and July plantings flowered in Salinas, Calif. The superior grade data for the new cultivar will be evident.

PRODUCTION AND GRADE DATA FROM PLANTINGS FLOWERED IN SALINAS, CALIF.

| Variety | Plant | Pinch | 1st cut | Peak flower | Prod. per sq. ft. | Crop, weeks | 7 grade | 5 grade | 3 grade | 1 grade | Total |
|---|---|---|---|---|---|---|---|---|---|---|---|
| Ocean Spray | 6/06 | 6/26 | 9/24 | 10/26 | 28.3 | 48 | 1.1 | 27.5 | 51.8 | 19.4 | 99.80 |
| White Elegance | 6/06 | 6/26 | 10/03 | 10/24 | 29.2 | 48 | .3 | 21.7 | 58.0 | 19.9 | 99.90 |
| Ocean Spray | 7/18 | 8/08 | 11/18 | 12/26 | 27.8 | 48 | 4.3 | 36.5 | 45.2 | 13.7 | 99.70 |
| White Elegance | 7/18 | 8/08 | 11/28 | 1/02 | 22.4 | 48 | 5.2 | 19.7 | 62.2 | 12.7 | 99.80 |
| Ocean Spray | 6/15 | 7/01 | 10/12 | 12/04 | 16.6 | 42 | .4 | 30.0 | 48.0 | 21.0 | 99.40 |
| White Elegance | 6/15 | 7/01 | 10/26 | 11/23 | 17.3 | 42 | 0 | 20.0 | 64.0 | 16.0 | 100.00 |

NOTE.—Grade date for Miniature or Spray Carnations based on American Carnation Society Standards. Key—7 grade=7+ flowers per stem; 5 grade=5+ flowers per stem; 3 grade=3+ flowers per stem; 1 grade=1+ flowers per stem.

I claim:

1. A new and distinct carnation cultivar characterized particularly as to uniqueness when compared to the cultivar White Elegance by its six to ten inches more vigor; stem length which averages two inches longer; two to four more flowers and buds per stem, which enables it to grade out 5–10% higher on the top two grades; approximately 7–10 days earlier flowering on the first crop; its well budded, open sprays during the winter months; two to five days longer keeping quality; its strong but pleasant fragrance; more fully petailed flowers, averaging approximately 50% more petals per flower; and its greater stem production per square foot for one-year crops planted after July 1 and into the winter months.

No references cited.

ROBERT E. BAGWILL, Primary Examiner